United States Patent [19]

Cymbalista

[11] Patent Number: 4,647,454

[45] Date of Patent: Mar. 3, 1987

[54] STABLE INTERFERON β COMPOSITION AND A METHOD OF STABILIZING INTERFERON β

[75] Inventor: Samuel Cymbalista, Jerusalem, Israel

[73] Assignee: Inter-Yeda Ltd., Israel

[21] Appl. No.: 475,177

[22] Filed: Mar. 14, 1983

[30] Foreign Application Priority Data

Mar. 17, 1982 [IL] Israel ............................................ 65277

[51] Int. Cl.$^4$ ...................... A61K 31/79; A61K 45/02
[52] U.S. Cl. ........................................ 424/80; 424/85
[58] Field of Search ................ 424/85, 80; 260/112 R

[56]  References Cited

U.S. PATENT DOCUMENTS

| | | | |
|---|---|---|---|
| 4,079,125 | 3/1978 | Sipos | 424/80 |
| 4,283,393 | 8/1981 | Field et al. | 424/180 |
| 4,301,146 | 11/1981 | Sanvordeker | 424/80 |

OTHER PUBLICATIONS

Merck Index, Windholz et al, editors Merck & Co, Inc., Rahway, N.J., p. 996, 1976.
Derwent Abstract, Japanese Pat. No. 55-102519, 1979.
Sedmak et al., Methods in Enzymology, vol. 78, pp. 591–595, 1981, Academic Press.
Van Damme et al., Methods in Enzymology, vol. 78, pp. 101–119, 1981, Academic Press.

*Primary Examiner*—Blondel Hazel
*Attorney, Agent, or Firm*—Ostrolenk, Faber, Gerb & Soffen

[57]  ABSTRACT

This disclosure relates to a method of stabilizing Human Fibroblast Interferon (HFIF) known as "Interferon β" with polyvinyl pyrrolidone and to transportable and storable vials containing such stabilized Interferon β.

13 Claims, No Drawings

STABLE INTERFERON β COMPOSITION AND A METHOD OF STABILIZING INTERFERON β

This invention relates to a method of stabilizing Human Fibroblast Interferon (HFIF) also known by the name and hereinafter designated as "Interferon β" and to stabilized Interferon β compositions which are transportable and storable for extended periods in closed vials as well as after resuspension in a suitable diluent.

Interferon β is a highly active, antiviral protein substance which is found in and obtained from certain human cells in minute quantities, as described in the pertinent literature. These quantities were insufficient for conducting the manifold clinical and other tests and studies necessary for evaluating the promising therapeutical properties of this substance.

Intensive efforts were therefore made by leading research institutes and drug companies the world over to find a method of producing larger quantities of Interferon β, mainly by tissue culture methods. As a result of these efforts, Interferon β is now available in commercial quantities. The Interferon β is purified and admixed with appropriate excipients, filtered, dispensed in glass vials, lyophilized, and sealed in vacuo, then stored at temperatures of −40° C. and shipped in dry ice.

It is known that the resulting Interferon β preparation is highly unstable and that it loses its biological activity within a relatively short period. All attempts made hitherto to stabilize Interferon β have failed.

It was thus unexpected and surprising when Applicants discovered that Interferon β preparations can be effectively stabilized by means of vinyl pyrrolidone polymer, hereinafter designated P.V.P., a polymer which has been known for a long time exclusively as a clarifying agent in wines and as a dispersing and suspending agent for pharmaceutical compositions. P.V.P. has molecular weights ranging from 10,000 to 700,000 and it is marketed under trademarks such as POVIDONE et al, (see "The Merck Index", 9th edition, page 7483 under No. 7498).

This invention relates to a novel stable Interferon composition comprised of Interferon β, conventional excipients, a buffer and vinyl pyrrolidone polymer, as a stabilizer.

This invention also relates to a method of stabilising Interferon β, wherein a highly purified Interferon β solution admixed with known excipients therefor is dialysed against an acetate buffer solution—pH=3.5, for about 48 hours, the resulting Interferon solution is subjected to sterile filtration, the filtrate is admixed with 0.5% to 10% weight/volume of polyvinyl pyrrolidone, dispensed into glass vials, lyophilized, whereupon the vials are sealed in vacuo and stored at 4° C.

The preferred excipients are mannitol and human serum albumin (HSA). The acetate buffer used contains sodium acetate and sufficient acetic acid to adjust the pH to 3.5 P.V.P. marketed as POVIDONE, having a molecular weight of about 50,000 is the preferred stabilizer, but P.V.P. having lower or higher molecular weights has also proved to be highly effective as a stabilizer, it is used in a final concentration of about 0.5 to 10% wt/volume of the preparation.

The preparation of the preferred inventive Interferon β composition will now be described in the following example.

EXAMPLE 20 lts of aqueous acetate buffer solution having a pH=3.5 are prepared by dissolving 21.6 cc of acetic acid and 4.02 gms of sodium acetate in the required volume of distilled water.

The inner surface of a sterile dialysis bag is wetted with sufficient concentrated human serum albumin to result in a 1% concentration in a highly purified Interferon β solution, having a specific activity of about $10^7$ international units per mg of protein, which is subjected to dialysis therein.

The resulting solution is dialysed against the acetate buffer of pH 3.5 and at a temperature of 4° C. for about 48 hours at a ratio of 1:100 Interferon solution to buffer solution with a change of the buffer solution after 24 hours.

The dialysed Interferon β preparation is admixed with mannitol 0.5% wt/volume final concentration and with P.V.P. at a 2% final concentration approximately prior to or following filtration through a sterile filter, previously impregnated with sufficient concentrated human serum albumin to raise the albumin concentration in the filtrate to 2% wt/volume. The filtrate is collected in a sterile bottle.

The P.V.P. concentration is then finally adjusted to 2% wt/volume and the concentration of mannitol to 0.5% wt/volume, if necessary. The final volume of the solution is adjusted with sterile acetate buffer.

2 cc each of the solution obtained are dispensed into sterile glass vials by means of a sterile Cornwall syringe, followed by lyophilization and the vials are then sealed in vacuo and stored at 4° C. The contents of the vials are resuspended by the addition of 2 cc of bidistilled sterile water.

The composition of the final product per vial is as follows:

| | |
|---|---|
| Sodium Acetate AG | 0.4 mgm |
| Sodium Chloride AG | 1.8 mgm |
| Human Serum Albumin Fraction V | 40.0 mgm |
| Mannitol AG | 10.0 mgm |
| PVP - Stabilizer | 40.0 mgm |
| Human Fibroblast Interferon | 1.0 $10^6$ I.U. (approximately) |

The effectiveness of P.V.P. of different molecular weights and in different concentrations on the stability of Interferon in its compositions will now be illustrated by the following tables 1 to 6 of which: Table (1) illustrates the effect of P.V.P. of molecular weight 24,000 at concentration ranging from 0.5% to 5% on the stability of Interferon in compositions immediately before and immediately after lyophilization and after storage for 1 to 4 months in sealed vials at 37° C.; The data in tables (2) and (3) illustrates the stability of the compositions under identical conditions, using P.V.P. of molecular weights 50,000 and 160,000 respectively, and comparative data are reported in these tables for Interferon β compositions without P.V.P. and compositions containing sucrose or Human Serum Albumin in various concentrations instead of P.V.P.; Tables (4), (5) and (6) illustrate the relationship between the titer of inventive Interferon β compositions and their content of P.V.P. of the same molecular weights as in tables (1), (2) and (3); (a) immediately after resuspension as hereinbefore described, and, (b) after storage of the resuspended compositions for 1 month at 4° C.

Comparative data for Interferon β compositions admixed with Sucrose or Human Serum albumin are again given.

The following data and remarks are essential for the understanding of these tables:

(a) The Human Fibroplast Interferon used in the compositions was initially purified to a specific activity ranging from $10^6$–$10^7$ international units per mg of protein.

2 to 4% although the use of PVP in concentration up to 10% also leads to positive stabilization results. Positive stabilization is also attained using PVP having molecular weights from 10,000 to 700,000.

Other modifications of the method described hereinabove are known to the man versed in the art and these are included herein provided that they fall within the ambit of the invention defined in the subsequent claims.

TABLE 1

Polyvinylpyrrolidone 24000

| Conc of PVP | Titer before Lyophilization | Titer after Lyophilization | Titer after 1 Month at 37° C. | Titer after 2 Months at 37° C. | Titer after 3 Months at 37° C. | Titer after 4 Months at 37° C. |
|---|---|---|---|---|---|---|
| 0% | 1.4 | 0.8 | 0.08 | 0.02 | <0.01 | <0.01 |
| 0.5% | 1.3 | 1.0 | 0.8 | 0.6 | 0.2 | 0.20 |
| 1% | 1.5 | 1.3 | 1.2 | 1.2 | 1.1 | 0.9 |
| 2% | 1.3 | 1.3 | 1.2 | 1.2 | 1.1 | 0.9 |
| 3% | 1.3 | 1.2 | 1.1 | 1.2 | 1.1 | 1.1 |
| 4% | 1.6 | 1.4 | 1.2 | 1.1 | 1.0 | 1.0 |
| 5% | 1.4 | 1.0 | 0.9 | 1.0 | 0.8 | 0.8 |
| 0 + Sucrose 5% | 1.5 | 0.7 | 0.05 | 0.01 | <0.01 | <0.01 |
| 0 + Sucrose 10% | 1.3 | 0.8 | 0.04 | 0.01 | <0.01 | <0.01 |
| 0 + HSA 3% | 1.4 | 0.8 | 0.1 | 0.03 | <0.01 | <0.01 |
| 0 + HSA 4% | 1.3 | 0.9 | 0.1 | 0.05 | 0.02 | 0.01 |

TABLE 2

Polyvinylpyrrolidone 50000

| Conc. of PVP | Titer before Lyophilization | Titer after Lyophilization | Titer after 1 Month at 37° C. | Titer after 2 Months 37° C. | Titer after 3 Months | Titer after 4 Months at 37° C. |
|---|---|---|---|---|---|---|
| 0 | 1.1 | 0.7 | 0.06 | 0.01 | <0.01 | <0.01 |
| 0.5% | 1.2 | 0.9 | 0.6 | 0.1 | 0.07 | 0.03 |
| 1% | 1.1 | 1.1 | 1.1 | 1.1 | 1.0 | 0.8 |
| 2% | 1.2 | 1.1 | 1.2 | 1.2 | 1.1 | 1.0 |
| 3% | 1.1 | 1.2 | 1.3 | 1.2 | 1.1 | 0.9 |
| 4% | 1.3 | 1.2 | 1.2 | 1.0 | 1.2 | 1.0 |
| 5% | 1.0 | 0.9 | 1.0 | 0.8 | 0.7 | 0.9 |
| 0 + Sucrose 5% | 1.1 | 0.6 | 0.07 | 0.02 | <0.01 | <0.01 |
| 0 + Sucrose 10% | 1.2 | 0.8 | 0.05 | 0.01 | <0.01 | <0.01 |
| 0 + HSA 3% | 1.2 | 0.8 | 0.09 | 0.03 | <0.01 | <0.01 |
| 0 + HSA 4% | 1.1 | 0.8 | 0.10 | 0.03 | 0.01 | <0.01 |

TABLE 3

Polyvinylpyrrolidone 160.000

| Conc of PVP | Titer before lyophilization | Titer after lyophilization | Titer after 1 Month at 37° C. | Titer after 2 Months at 37° C. | Titer after 3 Months 37° C. | Titer after 4 Months 37° C. |
|---|---|---|---|---|---|---|
| 0% | 1.5 | 0.8 | 0.05 | 0.01 | <0.01 | <0.01 |
| 0.5% | 1.4 | 1.0 | 0.09 | 0.06 | 0.05 | 0.03 |
| 1% | 1.6 | 1.3 | 1.0 | 0.6 | 0.6 | 0.6 |
| 2% | 1.4 | 1.6 | 1.5 | 1.3 | 1.4 | 1.3 |
| 3% | 1.5 | 1.5 | 1.3 | 1.4 | 1.3 | 1.2 |
| 4% | 1.6 | 1.4 | 1.3 | 1.4 | 1.3 | 1.2 |
| 5% | 1.7 | 1.3 | 1.4 | 1.3 | 1.2 | 1.2 |
| 0 + Sucrose 5% | 1.7 | 0.9 | 0.04 | 0.01 | <0.01 | <0.01 |
| 0 + Sucrose 10% | 1.3 | 0.8 | 0.05 | <0.01 | <0.01 | <0.01 |
| 0 + HSA 3% | 1.4 | 0.8 | 0.08 | 0.04 | <0.01 | <0.01 |
| 0 + HSA 4% | 1.5 | 1.0 | 0.1 | 0.05 | <0.01 | <0.01 |

(b) The data in the Tables relating to the titers of Interferon. in admixture with PVP in different concentrations are the averages of 6 titration results and the data are expressed in megaunits per vial.

(c) The difference in the initial titers of Interferon β are due to the use of Interferon from different batches which differ somewhat in their specific activity.

It is evident from the data reported in the tables that PVP of different molecular weight have maximal stabilizing effectiveness when used in concentration of from

TABLE 4

Polyvinyl pyrrolidone 24000

| Conc. of PVP | Titer of IF with resuspension | Titer of IF 1 Month after resuspension stored at 4° C. |
|---|---|---|
| 0% | 0.8 | <0.01 |
| 0.5% | 1.0 | 0.3 |
| 1% | 1.3 | 0.6 |
| 2% | 1.3 | 1.2 |
| 3% | 1.2 | 1.1 |

TABLE 4-continued

Polyvinyl pyrrolidone 24000

| Conc. of PVP | Titer of IF with resuspension | Titer of IF 1 Month after resuspension stored at 4° C. |
|---|---|---|
| 4% | 1.4 | 1.2 |
| 5% | 1.0 | 1.1 |
| 0 + Sucrose 5% | 0.7 | <0.01 |
| 0 + Sucrose 10% | 0.8 | <0.01 |
| 0 + HSA 3% | 0.8 | <0.01 |
| 0 + HSA 4% | 0.9 | <0.01 |

TABLE 5

Polyvinyl pyrrolidone 50000

| Conc of PVP | Titer of IF with resuspension | Titer of IF 1 Month after resuspension stored at 4° C. |
|---|---|---|
| 0% | 0.7 | <0.01 |
| 0.5% | 0.9 | 0.5 |
| 1% | 1.1 | 0.8 |
| 2% | 1.1 | 1.0 |
| 3% | 1.2 | 1.1 |
| 4% | 1.2 | 1.2 |
| 5% | 0.9 | 1.0 |
| 0 + Sucrose 5% | 0.6 | <0.01 |
| 0 + Sucrose 10% | 0.8 | <0.01 |
| 0 + HSA 3% | 0.8 | <0.01 |
| 0 + HSA 4% | 0.8 | 0.05 |

TABLE 6

Polyvinylpyrrolidone 160.000

| Conc. of PVP | Titer of IF with resuspension | Titer of IF 1 Month after resuspension stored at 4° C. |
|---|---|---|
| 0% | 0.8 | <0.01 |
| 0.5 | 1.0 | 0.3 |
| 1% | 1.3 | 0.8 |
| 2% | 1.6 | 1.4 |
| 3% | 1.5 | 1.3 |
| 4% | 1.4 | 1.4 |
| 5% | 1.3 | 1.3 |
| 0 + Sucrose 5% | 0.9 | <0.01 |
| 0 + Sucrose 10% | 0.8 | <0.01 |
| 0 + HSA 3% | 0.8 | <0.01 |
| 0 + HSA 4% | 1.0 | 0.03 |

I claim:

1. A stable Interferon $\beta$ composition comprising a buffered solution of highly purified Interferon $\beta$ and conventional excipients said solution being stabilized by 0.5 to 10% wt/volume of polyvinyl pyrrolidone.

2. A composition as claimed in claim 1, wherein the excipients are mannitol and human serum albumin.

3. A composition as claimed in claims 1 or 2, wherein the buffer is an acetate buffer having a pH of 3.5.

4. A composition as claimed in claims 1 or 2 packaged in a glass vial, lyophilized and sealed in vacuo.

5. A composition as claimed in claim 1 wherein the polyvinyl pyrrolidone has a molecular weight from 10,000 to 700,000.

6. A composition as claimed in claim 5 wherein the molecular weight is about 50,000.

7. A composition as claimed in claims 5 or 10 where the amount of polyvinyl pyrrolidone is 2 to 4%.

8. A method of stabilizing Interferon $\beta$, wherein a highly purified Interferon $\beta$ solution, admixed with known excipients therefor is dialysed against an acetate buffer solution, the resulting Interferon solution is admixed with 0.5 to 10% wt/volume of polyvinyl pyrrolidone prior to or following filtration through a sterile filter, dispensed into glass vials, lyophilized, and the vials are sealed in vacuo and stored at 4° C.

9. A method of stabilizing Interferon $\beta$ comprising admixing an Interferon $\beta$ solution with 0.5 to 10% wt/volume of polyvinyl pyrrolidone.

10. A method as claimed in claims 8 or 9 wherein the polyvinyl pyrrolidone has a molecular weight of 10,000 to 700,000.

11. A method as claimed in claim 10 wherein the polyvinyl pyrrolidone has a molecular weight of about 50,000.

12. A method as claimed in claim 10 wherein the amount of polyvinyl pyrrolidone is 2 to 4%.

13. A method as claimed in claims 8 or 9 wherein the amount of polyvinyl pyrrolidone is 2 to 4%.

* * * * *